United States Patent [19]

Crowley, Jr.

[11] Patent Number: 4,762,717

[45] Date of Patent: Aug. 9, 1988

[54] CONTINUOUS DELIVERY OF LUTEINIZING HORMONE RELEASING HORMONE COMPOSITIONS IN COMBINATION WITH SEX STEROID DELIVERY FOR USE AS A CONTRACEPTIVE

[75] Inventor: William F. Crowley, Jr., Newtonville, Mass.

[73] Assignee: The General Hospital Corporation, Boston, Mass.

[21] Appl. No.: 842,643

[22] Filed: Mar. 21, 1986

[51] Int. Cl.⁴ .............................................. A61F 2/00
[52] U.S. Cl. .................................... 424/425; 424/430; 424/432; 424/434; 424/433; 424/436; 424/464; 514/15; 514/800; 514/843
[58] Field of Search ................. 514/15, 843, 800, 874; 424/432, 434, 436, 430, 433, 425, 464

[56] References Cited

U.S. PATENT DOCUMENTS

| | | | |
|---|---|---|---|
| 3,822,355 | 7/1974 | Kincl | 424/243 |
| 3,836,651 | 9/1974 | Rudel et al. | 424/239 |
| 3,854,480 | 12/1974 | Zaffaroni et al. | 128/260 |
| 3,932,635 | 1/1976 | Segre | 424/239 |
| 3,939,264 | 2/1976 | Lachnit-Fixson | 424/239 |
| 3,942,641 | 3/1976 | Segre | 206/534 |
| 3,957,982 | 5/1976 | Lachnit-Fixson et al. | 424/238 |
| 3,969,502 | 7/1976 | Lachnit-Fixson | 424/239 |
| 4,008,209 | 2/1977 | Fujino et al. | 424/177 X |
| 4,010,125 | 3/1977 | Schally et al. | 260/8 |
| 4,010,149 | 3/1977 | Baba et al. | 260/112.5 LH |
| 4,010,256 | 3/1977 | Parlow | 424/88 |
| 4,012,496 | 3/1977 | Schopflin et al. | 424/15 |
| 4,072,668 | 2/1978 | Amoss et al. | 424/177 X |
| 4,083,967 | 4/1978 | Beddell et al. | 514/15 |
| 4,089,946 | 5/1978 | Foell et al. | 424/177 |
| 4,143,136 | 3/1979 | De Jage et al. | 424/240 |
| 4,215,038 | 7/1980 | Rivier et al. | 260/112.5 LH |
| 4,218,439 | 8/1980 | Rivier et al. | 427/177 |
| 4,234,571 | 11/1980 | Nestor et al. | 424/177 |
| 4,244,946 | 1/1981 | Rivier et al. | 424/177 |
| 4,263,282 | 4/1981 | von der Ohe et al. | 424/177 |
| 4,315,925 | 2/1982 | Hussain et al. | 514/843 X |
| 4,318,905 | 3/1982 | Nestor et al. | 424/177 |
| 4,338,305 | 7/1982 | Corbin | 424/177 |
| 4,341,767 | 7/1982 | Nestor et al. | 424/177 |
| 4,377,515 | 3/1983 | Veber et al. | 548/550 |
| 4,419,347 | 12/1983 | Nestor et al. | 424/177 |
| 4,481,190 | 11/1984 | Nestor et al. | 424/177 |
| 4,493,934 | 1/1985 | Veber et al. | 424/177 X |
| 4,504,414 | 3/1985 | Folkers et al. | 260/112.5 LH |
| 4,512,923 | 4/1985 | Flegel et al. | 260/112.5 LH |
| 4,530,839 | 7/1985 | Pasquale | 514/171 |
| 4,530,920 | 7/1985 | Nestor et al. | 514/15 |
| 4,544,554 | 10/1985 | Pasquale | 514/170 |
| 4,616,006 | 10/1986 | Pasquale | 514/170 |
| 4,621,079 | 11/1986 | Lachnit-Fixson et al. | 514/170 |
| 4,628,051 | 12/1986 | Pasquale | 514/170 |
| 4,666,885 | 5/1987 | Labrie | 514/15 |

FOREIGN PATENT DOCUMENTS

| | | | |
|---|---|---|---|
| 52/051012 | 4/1977 | Japan | 514/15 |

OTHER PUBLICATIONS

Kuhl, H. et al., *Clin. Endocrinology*, 21:179–188 (1984).
Lemay, A. et al., *Fertility Sterility*, 43:868–877 (1985).
Ryu, K. et al., *Contraception*, 27:605–617 (1983).
Crowley, S. F. et al., *N. Eng. J. Med.*, 302:1052–1057 (1980).
Crowley, W. F. et al., *J. Clin. Endo. Met.*, 52:370–372 (1981).
Nillius, S. J., *Clinics in Ob. Gyn.*, 11:551–572 (1984).
Marshall, J. C. et al., *J. Clin. Endocrin. Met.*, 49:712–718 (1979).
Jacobson, R. I. et al., *J. Clin. Endocrin. Met.*, 49:652–654 (1979).
Belchetz, P. E. et al., *Science*, 202:631–633 (1978).
Hausler, A. et al., *Fed. Proc.*, 38:1107 (1979).
Wildt, L. et al., *Fed. Proc.*, 38:978 (1977).
Crowley, W. F. et al., *J. Clin. Endocrin. Met.*, 51:173–175 (1980).
Crowley, W. F. et al., The Endocrine Society, Abstract (1980), presented at the Endocrine Society Meeting (1980).

Primary Examiner—Thurman K. Page
Attorney, Agent, or Firm—Saidman, Sterne, Kessler & Goldstein

[57] ABSTRACT

This invention is directed to a delivery system and a method useful for preventing pregnancy in female mammals by administering an LHRH composition. The method comprises administering during the entire follicular phase of the menstrual cycle, beginning at the time of menses, an LHRH composition and sufficient levels of an estrogenic steroid to counteract the possibility of side effects which may develop during prolonged therepy with LHRH. Following the follicular phase, at the beginning of the luteal phase, and for the entire course of the luteal phase, the LHRH/estrogenic steroid combination administered during the follicular phase, in combination with a physiological amount of progestational steroid, is administered.

The delivery system comprises means for administering the LHRH composition, estrogenic steroid and progestational steroid.

13 Claims, No Drawings

CONTINUOUS DELIVERY OF LUTEINIZING HORMONE RELEASING HORMONE COMPOSITIONS IN COMBINATION WITH SEX STEROID DELIVERY FOR USE AS A CONTRACEPTIVE

FIELD OF THE INVENTION

This invention relates to contraceptive methods for female mammals using luteinizing hormone releasing hormone (LHRH) compositions in combination with sex steroids. This invention also relates to delivery systems for the administration of the LHRH compositions in combination with sex steroids.

BACKGROUND OF THE INVENTION

Luteinizing hormone releasing hormone (LHRH), also referred to as gonadotropin releasing hormone (GnRH), produced in the hypothalamic region, stimulates the release of the gonadotropins, luteinizing hormone (LH) and follicle stimulating hormone (FSH) from the anterior pituitary gland. LH and FSH act on the gonads to stimulate the synthesis of steroid hormones and to stimulate gamete maturation. The release of LHRH, by stimulating the release of LH and FSH, controls the reproductive cycle in mammals.

Numerous LHRH analogues, both agonistic and antagonistic, have been synthesized. Low doses of LHRH and/or its agonistic analogues can stimulate ovulation and are useful in the treatment of hypothalamic and anovulatory infertility in the female due to hypothalamic deficiency in the synthesis or release, or both, of LHRH resulting in a hypogonal state. Additionally, these analogues stimulate spermatogenesis and androgen production in the male.

Paradoxically, larger doses of highly potent and long acting LHRH analogues have an opposite effect which blocks ovulation in the female and suppresses spermatogenesis and testosterone production in the male. Inhibitory (antagonistic) analogues of LHRH were developed for contraceptive purposes, by acting as a competetive inhibitor to endogenous LHRH at the pituitary receptor site. Nillius, S. J., "Luteinizing Hormone Releasing Hormone Analogues for Contraception," *Clinics in Ob. Gyn.* 11:551-572 (1984); Monroe, S. E. et al., "Ablation of Folliculogenesis in Women by a Single Dose of Gonadotropin-Releasing Hormone Agonist: Significance of Time in Cycle," *Fertility Sterility* 43:361-368 (1985); Lemay, A. L. et al., "Inhibition of Ovulation During Discontinuous Intranasal Luteinizing Hormone-Releasing Hormone Agonist Dosing in Combination with Gestagen-Induced Bleeding," *Fertility and Sterility* 43:868-877 (1985); Gudmundsson, J. A. et al., "Inhibition of Ovulation by Intranasal Nafarelin, A New Superactive Agonist of GnRH," *Contraception* 30: 107-114 (1984); and Kuhl, H. et al., "Contraception with an LHRH Agonist: Effect on Gonadotropin and Steroid Secretion Patterns," *Clinical Endocrin.* 21:179-188 (1984).

Administration of large doses of LHRH analogues produce a selective, reversible and complete biochemical castration at the pituitary level. These LHRH analogues have had several therapeutic applications in medicine. The first of these applications was their use in treating precocious puberty. Another application was their use to suppress uterine fibroids. In addition, prostate cancer, and other hormonally sensitive cancers, such as breast cancer, endometriosis, and polycystic ovarian disease all have proven to be suppressed during LHRH analogue administration. Filicori, M. et al., "A Conservative Approach to the Management of Uterine Leiomyoma: Pituitary Desentyation by an LHRH Analogue," *Am. J. Ob. Gyn.*, 6:726 (1983); Lemay, H. et al., "Reversible Hypogonadism Induced by a Luteinizing Hormone Releasing Hormone (LHRH) Agonist (Buserelin) as a New Therapeutic Approach for Endometriosis," *Fertil. Steril.*, 41:863 (1984); Schriock, E. et al., "Treatment of Endometriosis with a Potent Agonist of Gonadotropin-Releasing Hormone (Nafarelin)," *Fertil. Steril.*, 44:583; and Chang, R. J. et al., "Steroid Secretors in Polycytic Ovarian Disease after Ovarian Suppression by a Long-Acting Gonadotropin-Releasing Hormone Agonist," *J. Chem. Endomel. Metab.*, 56:897 (1983).

The central problem now emerging with this prolonged treatment relates to the nearly total biochemical castration produced by these LHRH analogues. The pituitary quiescence induced by LHRH analogues results in a total suppression of gonadotropins and ovarian steroid secretions (estrodiol and progesterone). This pituitary quiescence in women leads to the side effects of estrogen deficiency, including hot flashes, vaginal dryness, and, most ominously, the possibility of osteopenia and osteoporosis. These side effects seen with prolonged LHRH therapy are thus comparable to those seen in menopausal women with a similar degree of estrogen deficiency. Unfortunately, these long term side effects of using LHRH analogues may limit their widespread applicability as contraceptives. Thus, it would be desirable to have a contraceptive using LHRH and/or its analogues (either agonists and/or antagonists) that can be administered in a safe, physiologic, and convenient mechanism, without the side effects relating to deprivation of the sex steroid hormones.

SUMMARY OF THE INVENTION

This invention is directed to a method of preventing pregnancy in mammals by administering luteinizing hormone releasing hormone (LHRH), LHRH analogues, LHRH agonists, and/or LHRH antagonist in a first delivery system which is combined with continuous administration of an effective amount of estrogenic steroids during the follicular phase of the menstrual cycle, beginning at the onset of normal menses. Then a second delivery system is administered during the luteal phase of the menstrual cycle until the onset of normal menses. This second delivery system comprises the LHRH/estrogenic steroid combination, as described above, and additionally provides an effective dosage of a progestational steroid.

The invention further comprises a delivery system comprising a first delivery system for sequential administration to a female mammal during the follicular phase of the menstrual cycle beginning at the onset of menstruation, an effective amount of an LHRH composition and an effective amount of estrogenic steroid; and a second delivery system for administration to the female during the luteal phase of the menstrual cycle, an effective amount of an LHRH analogue, an effective amount of estrogenic steroid, and an effective amount of progestational steroid.

This method and the delivery system provide continuous suppression of pituitary gonadotropin secretion by sequential administration of LHRH, LHRH analogues, LHRH agonists and/or LHRH antagonists, thus inhibiting ovulation. Further, this invention permits the sequential application of estrogenic and progestational sex steroids in a sequence designed to mimic the physiologic secretion of steroids in the menstrual cycle. By this invention, the side effects of prolonged LHRH therapy resulting from indirectly induced estrogen deficiency are avoided.

DESCRIPTION OF THE PREFERRED EMBODIMENTS

This invention is directed to a method of preventing pregnancy in mammals comprising administration through a first delivery system an effective amount of luteinizing hormone releasing hormone (LHRH), LHRH analogues, LHRH agonists and/or LHRH antagonists (hereinafter referred to as "LHRH compositions") and an effective amount of an estrogenic steroid during the follicular phase of the menstrual cycle, beginning at the onset of normal menses. The method then comprises replacing the first delivery system at the end of the follicular phase with a second delivery system. The second delivery system administers an LHRH composition, an effective dosage of estrogenic steroid, and an effective dosage of progestational steroid to the female during the luteal phase of the menstrual cycle. Following the administration of the second delivery system, the first delivery system is readministered, at which time menstruation would typically occur. The two delivery systems are thus sequentially administered at approximately the beginning of the follicular phase and at approximately the beginning of the luteal phase of the menstrual cycle.

"LHRH composition" is used herein to describe luteinizing hormone releasing hormone (LHRH), LHRH analogues, LHRH agonists and LHRH antagonists. The LHRH compositions that may be used in this invention are physiologically active peptides and are gonadotropin secretory inhibitors or gonadotropin-effect blockers. LHRH is characterized as a decapeptide having the following structure:

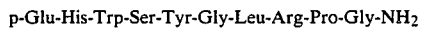

p-Glu-His-Trp-Ser-Tyr-Gly-Leu-Arg-Pro-Gly-NH$_2$

LHRH agonist and LHRH antagonist refer to such physiologically active peptides which respectively enhance or inhibit the biological activity of LHRH. LHRH, LHRH analogues, LHRH agonists and LHRH antagonists are well known in the art and are described in numerous patents, including the following patents: U.S. Pat. Nos. 4,530,920; 4,481,190; 4,419,347; 4,341,767; 4,318,905; 4,234,571; 4,386,074; 4,244,946; 4,218,439; 4,215,038; 4,072,668; 4,431,635; 4,317,815; 4,010,125; 4,504,414; 4,493,934; 4,377,515; 4,504,414; 4,338,305; 4,089,946; 4,111,923; 4,512,923; 4,008,209; and 4,010,149, all incorporated herein by reference. The LHRH compositions described in the above patents may be used in the methods of this invention.

As used herein, estrogenic and progestational steroids refer to both the natural and synthetic compositions for these sex steroids. These hormones are well known in the art and are described in *Remington's Pharamaceutical Sciences* (16th edition 1980) at pages 925–939.

Estrogenic steroids which can be used according to the inventions described herein include natural estrogenic hormones and congeners, including, but not limited to, estradiol, estradiol benzoate, estradiol cypionate, estradiol valerate, estrone, piperazine estrone sulfate, ethinyl estradiol, polyestradiol phosphate, estriol, and estrone potassium sulfate. Synthetic estrogens can be used in the inventions, including, but not limited to, benzestrol, chlorotrianisene, dienestrol, diethystilbestrol, diethylstilbestrol diphosphate, and mestranol. In the preferred embodiment of this invention, natural estrogenic hormones are used.

Also included are estrogens developed for veterinary use, including equine estrogens such as equilelinin, equilelinin sulfate and estetrol.

Typical dose ranges for estrogenic steroids will depend upon the estrogenic steroid compound chosen for use in this invention and the female mammal patient. For a human adult female, typical dose ranges will be administered such that the serum level of estradiol will be from about 50 to about 140 pq/ml. Preferably the serum level of estradiol is from about 20 to about 150 pg/ml; more preferably from about 80 to about 120 pg/ml.

Progestational steroids which can be used according to the inventions described herein include, but are not limited to, dydrogesterone, ethynodiol diacetate, hydroxyprogesterone caproate, medroxyprogesterone acetate, norethindrone, norethindrone acetate, norethynodrel, norgestrel, progesterone, and megestrol acetate.

Veterinarian progestational steroids can also be used in this invention, including acetoxyprogesterone, chlormadinone acetate, delmadinone acetate, proliges-terone, melengestrol acetate, and megestrol acetate.

Typical dose ranges for progestational steroids will also depend upon the progestational steroid chosen for use in this invention and upon the female mammal patient. For a human adult female, typical dose ranges will be an amount which can be administered such that the patient's serum levels of progesterone will be from about 1 to about 20 ng/ml. Preferably the serum level of progesterone is from about 1 to about 15 ng/ml; more preferably from about 2 to about 10 ng/ml.

In the combined administration of an effective dose of LHRH composition, the dose range will depend upon the particular LHRH composition used, but will be in an amount sufficient to suppress LH and FSH by the action of the LHRH composition on the pituitary membrane receptor. As will be understood by one of skill in the art, the effective dose ranges will be compound specific and will depend upon patient characteristics, such as age and weight. Further, the effective amount of LHRH composition will also depend upon the route of administration. Thus, administration by oral, subcutaneous, intramuscular, and intravenous routes will typically require less LHRH composition than administration by nasal, aural, transdermal, or vaginal routes. An effective dose range of LHRH composition may be determined by routine testing by one of skill in the art, without undue experimentation. Further, the LHRH composition may comprise one LHRH composition or may comprise two or more LHRH compositions. In general, it is expedient to administer the active LHRH composition in amounts between about 0.01 to 10 mg/kg of body weight per day. It will be understood in the art that this range will vary depending upon whether a LHRH antagonistic analogue or a LHRH agonistic analogue, or a combination of the two, is administered.

As is known in the art, menstrual cycles are characteristic of humans and primates and do not occur in other vertebrate groups. Other mammals have estrous cycles. Both menstrual cycles and estrous cycles are regulated by the same interaction of the hypothalmic, pituitary and ovarian hormones, and the effects of the ovarian hormones on the reproductive tract are comparable. The menstrual cycle is generally divided into two phases: the follicular phase and the luteal phase. The follicular phase extends from the onset of menstruation to ovulation (approximately 14 days in humans). The luteal phase extends from ovulation to the beginning of menstruation (approximately another 14 days in humans).

The estrous cycle is generally divided into four phases: the estrus phase, the metestrus phase, the diestrus phase, and the proestrus phase. Ovulation typically occurs during the estrus phase and thus the estrus and metestrus phases roughly correspond to the luteal phase. The diestrus phase and proestrus phase roughly correspond to the follicular phase. As used herein, these phases are all referred to as follicular and luteal phases of the menstrual cycle, although it is to be understood that the inventions described herein also apply to mammals with estrous cycles. Appropriate dose ranges can be determined for mammals with estrous cycles by one of skill in the art through routine testing, without undue experimentation. In mammals with estrous cycles, it may also be desirable to control estrous behavior. The dose range administered for prevention of pregnancy and reduction of estrous behavior can also be determined by one of skill in the art by routine testing.

The method of this invention may be administered to mammals including but not limited to humans, primates, equines, canines, felines, bovines, and ursines.

LHRH compositions are absorbed very well across a wide variety of surfaces. Thus oral, subcutaneous, intramuscular, intravenous, vaginal, nasal, transdermal and aural routes of administration have all proven to be effective. In one embodiment of this invention, administration of the delivery system is made via the vaginal route. Approximately 10% of the LHRH composition is absorbed through the vaginal route. Thus, the LHRH composition is administered via a vaginal delivery system using a matrix which permits slow degradation of the LHRH composition and transvaginal absorption. In this same first vaginal delivery system an effective dosage of physiological amounts of an estrogenic steroid is also delivered. This delivery system allows complete suppression of gonadotropins, removal of reproductive function of the ovaries, total suppression of ovarian steroidogenesis, and yet still effects a physiological replacement of sufficient levels of estrogen to thwart the long term side effects of LHRH administration. This first vaginal delivery system is administered during the follicular phase of the menstrual cycle, beginning at the onset of normal menses.

Following maintenance of the LHRH/estrogenic steroid delivery system during the follicular phase (typically fourteen days in humans), this first delivery system is replaced by a second vaginal delivery system which has the LHRH/estrogenic steroid combination and an effective physiological amount of a progestational steroid. This second delivery system is administered during the luteal phase of the menstrual cycle (typically fourteen days in humans), until the onset of normal menses. This second delivery system provides an artificial luteal phase to the females.

Following the second vaginal delivery system, and readministration of the first vaginal delivery system, menstruation occurs, reassuring the patient of lack of conception. Further, the administration of a progestational steroid in the second delivery system permitting menstruation, also avoids endometrial hyperplasia.

The matrix carrier vehicle may be one of a known class material suitable for use with the controlled release of the foregoing compositions in the physiological environment of the vagina. Typical examples include polymeric diffusion material, such as those described in U.S. Pat. Nos. 4,012,496 and 3,854,480, incorporated herein by reference.

The invention further comprises a delivery system comprising a first delivery system for administration to a female mammal, during the follicular phase of the menstrual cycle beginning at the onset of menstruation, of an effective amount of an LHRH composition and an effective amount of estrogenic steroid; and a second delivery system for administration to the female during the luteal phase of the menstrual cycle, of an effective amount of an LHRH composition, an effective amount of estrogenic steroid, and an effective amount of progestational steroid.

This delivery system comprises an apparatus or device for administering the LHRH composition, estrogenic steroid, and progestational steroid. Typical apparati or devices that can be used in this invention include rings, suppositories, other surface-active devices for transvaginal administration of the compounds.

The delivery system according to this invention can also comprise a drug delivery system comprising two formulations: the first formulation comprises a LHRH composition and estrogenic steroid and the second formulation comprises a LHRH composition, an estrogenic steroid, and a progestational steroid. These formulations can be in the form of a tablet for oral administration. These formulations can also be in the form of a suspension or aerosol for subcutaneous, intramuscular, intravenous, nasal, and aural routes of administration. For transdermal administration, it is preferred that the formulation be in the form of a cream for topical administration by which the active ingredients can be absorbed through the skin. All of the foregoing formulations may be prepared by any of the methods well-known in the pharmaceutical art, for example, as described in *Remington's Pharmaceutical Sciences* (16th edition, 1980).

The following examples describe the materials and methods that may be used in carrying out the invention. The examples are not intended to limit the invention in any manner.

EXAMPLES

The following are summary examples of delivery systems for use with the method of this invention, each in a 28 day administration cycle.

EXAMPLE 1

An adult female human patient seeking contraceptive means to prevent pregnancy is provided with the following treatment:

In the follicular phase, beginning with the onset of menstruation, the first delivery system administers an LHRH composition and a natural estrogenic steroid, such that the amount of LHRH suppresses LH and FSH secretion during the entire period of administration, and the serum level of estrogen is maintained at from about 20 to about 120 pg/ml.

The first delivery system is replaced after 14 days, the beginning of the luteal phase, with a second delivery system. The second delivery system administers an LHRH composition, a natural estrogenic steroid, and a progestational steroid, such that, during the entire period, the amount of LHRH suppresses LH and FSH; the serum level of estrogen is maintained at from about 20 to about 120 pg/ml; and the serum level of progesterone is maintained at from about 1 to 10 ng/ml.

The second delivery system is removed after 14 days, typically the beginning of menstruation. The first delivery system is then re-administered. Thus, there is a sequential administration of the first and second delivery systems designed to inhibit ovulation while supplying sex steroids in amounts associated with physiologic levels encountered during normal menstrual function.

EXAMPLE 2

The following Table 1 shows the structure of decapeptide LHRH and some of its potent agonists and antagonists which may be administered in the delivery system described in Example 1.

TABLE 1

Structures of LHRH and Potent Agonists and Antagonists

| | Agonist | | | | | Antagonist | |
|---|---|---|---|---|---|---|---|
| I | II Buserelin | III Naferelin | IV | LH—RH | I | II | III |
| — | — | — | | Pyro—Glu | Ac—$\Delta^2$-Pro | NAc—D-p-Cl—Phe | |
| | | | | His | p-F—D-Phe | NAc—D-p-Cl—Phe | D-Phe |
| | | | | Trp | D-Trp | D-Trp | D-Trp |
| | | | | Ser | | | |
| | | | | Tyr | | | |
| D-Trp | D-Ser(TBU) | D(NAL2) | D-His(imBzl) | Gly | D-Trp | D-Phe | D-Phe |
| | | | | Leu | | | |
| | | | | Arg | | | |
| | | | Pro—NEt | Pro | | | |
| EA* | EA* | — | | Gly—$NH_2$ | — | D-Ala | — |

*EA = des—Gly—$NH_2$10-ethylamide.

The foregoing invention has been described in some detail by illustration and example for purposes of clarity and understanding. It would be obvious that certain changes and modifications may be practiced within the scope of the invention, as limited only by the scope of the appended claims.

What is claimed is:

1. A delivery system for preventing pregnancy in a female mammal, comprising for sequential administration first and second delivery systems,
   said first delivery system for administration to said mammal during the follicular phase of the menstrual cycle, of an effective amount of a luteinizing hormone releasing hormone (LHRH) composition and an effective amount of an estrogenic steroid; and
   said second delivery system for administration to said mammal during the luteal phase of the menstrual cycle, an effective amount of a luteinizing hormone releasing hormone (LHRH) composition, an effective amount of an estrogenic steroid, and an effective amount of progestational steroid.

2. A delivery system according to claim 1 wherein said administration of said first or second delivery systems is selected from the group consisting of oral, subcutaneous, intramuscular, intravenous, vaginal, nasal, transdermal or aural routes of administration.

3. The delivery system according to claim 2 wherein said administration of said first or second delivery systems is by vaginal route of administration.

4. A delivery system according to claim 1 wherein said first or second delivery systems are in the form of a tablet.

5. A delivery system according to claim 1 wherein said first or second delivery systems are in the form of a suspension.

6. A delivery system according to claim 1, wherein said first or second delivery systems are in a transdermal form.

7. A delivery system according to claim 1 wherein said first or second delivery systems are in the form of a vaginal ring or suppository.

8. A method for preventing pregnancy in a female mammal, comprising:
   (a) administering via a first delivery system an effective amount of a luteinizing hormone releasing hormone (LHRH) composition and an effective amount of an estrogenic steroid to said female during the follicular phase of the menstrual cycle, beginning at the onset of normal menses in said female and,
   (b) replacing said first delivery system at the end of said follicular phase with a second delivery system, wherein said second delivery system administers a luteinizing hormone releasing hormone (LHRH) composition, an effective amount of an estrogenic steroid and an effective amount of a progestational steroid to said female during the luteal phase of the menstrual cycle, until the beginning of normal menses in said female.

9. The method according to claim 8 wherein said female mammal comprises a human female.

10. The method according to claim 8 wherein said administration of said first or second delivery system is selected from the group consisting of oral, subcutaneous, intramuscular, intravenous, vaginal, nasal, transdermal or aural routes of administration.

11. The method according to claim 8 wherein said route of administration is by vaginal means.

12. The method according to claim 11 wherein said vaginal means is by a vaginal ring delivery system.

13. The method according to claim 11 wherein said vaginal means is by a suppository.

* * * * *